(12) United States Patent
Hohmann et al.

(10) Patent No.: US 7,344,855 B2
(45) Date of Patent: Mar. 18, 2008

(54) FERMENTATION PROCESS

(75) Inventors: Hans-Peter Hohmann, Lörrach (DE); Nigel John Mouncey, Binningen (CH); Uwe Sauer, Zürich (CH); Nicola Zamboni, Losone (CH)

(73) Assignee: DSM IP Assets B.V., Heerlen (NL)

(*) Notice: Subject to any disclaimer, the term of this patent is extended or adjusted under 35 U.S.C. 154(b) by 0 days.

(21) Appl. No.: 10/505,855

(22) PCT Filed: Feb. 20, 2003

(86) PCT No.: PCT/EP03/01714

§ 371 (c)(1), (2), (4) Date: Aug. 26, 2004

(87) PCT Pub. No.: WO03/072785

PCT Pub. Date: Sep. 4, 2003

(65) Prior Publication Data

US 2005/0124030 A1 Jun. 9, 2005

(30) Foreign Application Priority Data

Feb. 27, 2002 (EP) .................. 02004499

(51) Int. Cl.
C12P 25/00 (2006.01)
C12N 1/21 (2006.01)
C07H 21/04 (2006.01)

(52) U.S. Cl. .............. 435/66; 435/252.3; 435/252.31; 435/69.1; 435/189; 536/23.2

(58) Field of Classification Search .............. 435/91.1, 435/109

See application file for complete search history.

(56) References Cited

U.S. PATENT DOCUMENTS

2004/0180408 A1* 9/2004 Pompejus et al. ......... 435/69.1

FOREIGN PATENT DOCUMENTS

| EP | 0 405 370 | 1/1991 |
|---|---|---|
| EP | 1 103 603 | 5/2001 |
| EP | 1 170 376 | 1/2002 |
| WO | WO 98/02552 | 1/1998 |
| WO | WO 01/48225 | 7/2001 |

OTHER PUBLICATIONS

Calhoun, M. W. et al., Energetic Efficiency of *Escherichia coli*: Effects of Mutations in Components of the Aerobic Respiratory Chain, *J. of Bacteriology*, vol. 175, No. 10, pp. 3020-3025 (1993).
Winstedt, L. et al., Cytochrome bd Biosynthesis in *Bacillus subtilis*: Characterization of the cydABCD Operon, *J. of Bacteriology*, vol. 180, No. 24, pp. 6571-6580 (1998).
Kusumoto, K. et al., "Menaquinol Oxidase Activity and Primary Structure of Cytochrome bd From the Amino-Acid Fermenting Bacterium *Corynebacterium glutamicum*," *Arch. Microbiol.*, vol. 173, pp. 390-397 (2000).
Kunsl, F. et al., "*Bacillus subtilis* Complete Genome (section 20 of 21): From 3809641 to 4010779," *Database EMBL Online*, Database Accession No. Z99123; AL009126, Nov. 20, 1997.

* cited by examiner

*Primary Examiner*—Rebecca E. Prouty
*Assistant Examiner*—M. Y. Meah
(74) *Attorney, Agent, or Firm*—Bryan Cave LLP

(57) ABSTRACT

A process for the preparation of a target fermentation product comprising cultivation of an aerobic microorganism to produce such product, wherein in the microorganism the efficiency of the respiratory chain is increased, transformed and novel nucleotide sequences.

8 Claims, No Drawings

SEQUENCE LISTING

```
<160> NUMBER OF SEQ ID NOS: 5

<210> SEQ ID NO 1
<211> LENGTH: 3560
<212> TYPE: DNA
<213> ORGANISM: Artificial
<220> FEATURE:
<221> NAME/KEY: misc_feature
<222> LOCATION: (1)..(3560)
<223> OTHER INFORMATION: plasmid pNMR21

<400> SEQUENCE: 1
ccgatgtcta tcgggcttgt gtttatggtt gcgttgatgg agactcttta tcttgtaaag      60
aaaaatgagc tgtatctcaa aatggcaaag ttttggggac acttattctt aataaatttc     120
gcagtcggtg ttgtaacggg gattttgcaa gaattccagt ttggactgaa ctggtcagat     180
tactcccgtt ttgtcggaga tgtatttggc gctccgcttg cgattgaagc attattggcg     240
tttttcatgg aatctatttt tatcggatta tggattttg gctgggaccg cctgccgaag      300
aaaattcacg cgctctgcat atggctcgta tcattcggaa cgatcatgtc atctttctgg     360
attttaacag caaactcctt tatgcaggag ccggtcggct ttacgatcaa aaacggccgc     420
gcggaaatga atgattttgg cgcgttgatt acaaaccctc agctttgggt tgaattcccg     480
cacgttattt tcggtgcgct tgccactgga gctttcttta ttgccggagt gagtgctttt     540
```

```
aaactgctga agaaaaaaga agtgccgttc tttaagcaat cttttaaact cgcaatgatc    600
gtcggtcttt gtgccggtct tggcgtcggc cttagcggac acatgcaggc tgagcacttg    660
atggaatcac agccgatgaa aatggctgcc agtgaaggcc tatgggaaga cagcggtgac    720
cctgctgctt ggaccgcttt tgcgacgatc gatacaaaaa atgaaaaaag ctcaaatgaa    780
atcaaagttc cttatgcctt gagctacttg gcttatcaga aattcagcgg aagtgtcaaa    840
gggatgaaaa cccttcaggc tgagtacgaa aaaatatacg gaaaaggcga ctacattccg    900
ccagtgaaaa cgacattctg gagcttccgc atcatggtag gagcaggtgt tgtcatgatt    960
cttgctgcgt taggcggcct ttggttaaac cgccgtaaaa agcttgaaaa cagcaaatgg   1020
tatttgcgca tcatgatcgc gttgatttcc ttcccgtttc ttgcaaactc cgcgggctgg   1080
attatgacag aaatcggacg tcagccttgg acggttatgg ggttaatgac aaccgctcaa   1140
tctgtgtcgc taacgtaac agcgggttcc ttgttattct caatcatcgc attcggtgtg   1200
atgtacatga ttcttggtgc actgcttgtc ttcttgttta ccgtgagat taaaaaaggt   1260 gcggagcatg ataatcatca tgatgtgcct gtatcaacag atccatttag tcaggaggta   1320
taccatggca tctcttcatg atctttggtt tatactcgtt gctgtattgt ttgtaggatt   1380
cttctttttg gaaggctttg atttcggggt cggcatggcg acccgttttc ttggccataa   1440
tgaattagaa cgcagagtgc tgatcagctt gggcagcagg tcgagatcag gaatgagtt   1500 tataaaataa aaaagcacc tgaaaaggtg tctttttttg atggttttga acttgttctt   1560
tcttatcttg atacatatag aaataacgtc attttattt tagttgctga aaggtgcgtt   1620
gaagtgttgg tatgtatgtg ttttaaagta ttgaaaaccc ttaaaattgg ttgcacagaa   1680
aaaccccatc tgttaaagtt ataagtgact aaacaaataa ctaaatagat gggggtttct   1740
tttaatatta tgtgtcctaa tagtagcatt tattcagatg aaaaatcaag ggttttagtg   1800
gacaagacaa aaagtggaaa agtgagacca tgtgcttagg aagacgagtt attaatagct   1860
gaataagaac ggtgctctcc aaatattctt atttagaaaa gcaaatctaa aattatctga   1920
aaagggaatg agaatagtga atggaccaat aataatgact agagaagaaa gaatgaagat   1980
tgttcatgaa attaaggaac gaatattgga taaatatggg gatgatgtta aggctattgg   2040
tgtttatggc tctcttggtc gtcagactga tgggccctat tcggatattg agatgatgtg   2100
tgtcatgtca acagaggaag cagagttcag ccatgaatgg acaaccggtg agtggaaggt   2160
ggaagtgaat tttgatagcg aagagattct actagattat gcatctcagg tggaatcaga   2220
ttggccgctt acacatggtc aattttttctc tattttgccg atttatgatt caggtggata   2280
cttagagaaa gtgtatcaaa ctgctaaatc ggtagaagcc caaacgttcc acgatgcgat   2340 ttgtgcccott atcgtagaag agctgtttga atatgcaggc aaatggcgta atattcgtgt   2400
gcaaggaccg acaacatttc taccatcctt gactgtacag gtagcaatgg caggtgccat   2460
gttgattggt ctgcatcatc gcatctgtta tacgacgagc gcttcggtct taactgaagc   2520
agttaagcaa tcagatcttc cttcaggtta tgaccatctg tgccagttcg taatgtctgg   2580
tcaactttcc gactctgaga aacttctgga atcgctagag aatttctgga atgggattca   2640
ggagtggaca gaacgacacg gatatatagt ggatgtgtca aaacgcatac cattttgaat   2700
gatcatcttt atgattctcc tcggccttgt cgcgcagaga aaagcggatc gtcagtgaa   2760 atcctatcag agactttcca atcattttgt tgattctctt cgcgggctgg agacattgcg   2820
tttcctaggt ttgagcaagt cacacagcaa aaatattttc tatgtgagtg agcggtatcg   2880
caaggcaacg atgagcacac tccgggtggc gttttttgtca tcattcgccc tcgatttttt   2940
```

-continued

| | |
|---|---|
| cacgatgctg tcggtggcga cagtcgcagt atttctgggc ctgcgcctca ttgacggcga | 3000 |
| tattttgctt ggccctgctt taacggcgct tattctggcg cctgagtatt ttttgccggt | 3060 |
| gcgggaagtg gggaatgatt atcatgcaac gctgaacggc caggaagcag gaaaaaccat | 3120 |
| tcaagagatt ttgtcgcagc ctggttttaa agaagagacg ccgcttcagc tcgaagcttg | 3180 |
| gtccgatcag gatgagctga agctgtcagg cgtgtcagtc ggccgttcgg tgtctgatat | 3240 |
| tcatctctca ttcaaaggca agaaaaaaat cggcattatc ggtgcaagcg gcgccggaaa | 3300 |
| atcaacatta attgatattc tcggcggatt tttagagccg gatggcggga tgattgaggt | 3360 |
| taatggtaca agccggtccc atttgcagga cggcagctgg cagaagaacc ttctttacat | 3420 |
| tccccagcat ccgtacattt ttgatgatac gcttggcaac aacattcgct tctaccatcc | 3480 |
| aagcgcttcg gcagaggata caacacgtgc tgctgcctca gcgggactga cggagctggt | 3540 |
| gaacaacctt cctgacggat | 3560 |

```
<210> SEQ ID NO 2
<211> LENGTH: 24
<212> TYPE: DNA
<213> ORGANISM: Artificial
<220> FEATURE:
<221> NAME/KEY: misc_feature
<222> LOCATION: (1)..(24)
<223> OTHER INFORMATION: primer CydA+1

<400> SEQUENCE: 2
gagaggatcc gatgtctatc gggc                                          24

<210> SEQ ID NO 3
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: primer CydC-1

<400> SEQUENCE: 3
gcgcggatcc gtcaggaagg                                               20

<210> SEQ ID NO 4
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: primer pBESTBcl+1

<400> SEQUENCE: 4
gagatgatca gcttgggcag caggtcg                                       27

<210> SEQ ID NO 5
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: primer pBESTBcl-1

<400> SEQUENCE: 5
gagatgatca ttcaaaatgg tatgcg                                        26
```

FERMENTATION PROCESS

This application is the National Stage of International Application No. PCT/EP03/01714, filed Feb. 20, 2003.

The present invention relates to a process for the preparation of a target fermentation pro-duct, to transformed microorganisms and to novel nucleotide sequences.

More particularly, the present invention provides a process for the preparation of a target fermentation product comprising cultivation of an aerobic microorganism to produce such product, wherein in the microorganism the efficiency of the respiratory chain is increased.

Under aerobic conditions, generation of cellular energy in the form of adenosine triphos-phate (ATP) occurs primarily by respiration, in which the electron flow from the reduced form of an electron carrier like NADH or FMNH2 to oxygen is coupled to proton trans-location across the cytoplasmic membrane. Respiration involves a set of membrane-associated compounds referred to as "respiratory chain" which are capable of being reversibly oxidized and reduced. Many organisms, including *Escherichia, Bacillus, Cyanobacter, Streptomyces,* and *Corynebacterium,* e.g. *E. coli, B. subtilis, B. amyloliquefaciens, B. licheni-formis, B. ammoniagenes,* and *C. glutamicum,* have the ability to switch between alternative subchains of the respiratory chain. These sub-chains have a common component, i.e. ubi-quinone or menaquinone, but different terminal oxidases. The respiratory chain of, e.g., *Bacillus subtilis* branches into the cytochrome C oxidase subchain and the quinol oxidase subchain. The terminal oxidase of the cytochrome C oxidase subchain is cytochrome aa3 oxidase encoded by ctaCDEF. The terminal oxidase of the quinol oxidase subchain is either cytochrome aa3 oxidase or cytochrome bd oxidase, encoded by qoxABCD and cydAB, res-pectively. In *C. glutanlicum* at least two subchains of the respiratory chain are present. One subchain consists of the cytochrome bc1c complex encoded by qcrABC and the cytochrome aa3 oxidase encoded by ctaCDE. The other subchain consists of cytochrome bd oxidase en-coded by cydAB.

The degree of coupling between electron flow and proton translocation and, thus, energe-tic efficiency differs between the subchains, not only between the subchains as a whole but also between particular components of a subchain. For example, the above cytochrome aa3 oxidase is more efficient than the above cytochrome bd oxidase, i.e. more protons are translocated per electron when cytochrome aa3 oxidase is involved. Naturally, cells utilise that subchain of the respiratory chain that is best suited for growth under given environ-mental conditions.

To increase the efficiency of the respiratory chain a more energy efficient component of the respiratory chain may be introduced or, particularly in microorganisms having a natural capability to utilize alternative subchains of the respiratory chain, expression of a less ener-gy efficient component of a subchain may be prevented or reduced, thus directing the elec-tron flow to the more efficient subchain.

Examples for a microorganism having a natural capability to utilize alternative subchains of the respiratory chain which may be used in the process of the invention include mem-bers of the genera mentioned above.

As used herein, the term "a component of the respiratory chain is introduced" refers to the introduction of a suitable polynucleotide sequence encoding said component into a micro-organism and the recombination of the polynucle-otide sequence with the genomic DNA of the microorganism by a single or double cross-over mechanism. The polynucle-otide may contain transcriptional and translational signals, e.g. a promoter sequence and a ribosomal binding site, which are linked to the gene encoding said component so as to allow expres-sion of the component. For convenient selection of transformants of the microorganism containing the polynucleotide sequence genes encoding an antibiotic resistance marker or a gene complementing a possible auxotrophy of the microorganism may be encoded by the polynucleotide sequence as well. Furthermore, the polynucleotide may contain at the 5' and/or 3' end DNA sequences of, e.g. at least 50 base pairs in length from the locus at which the polynucleotide sequence is to be introduced into the genome of the micro-organism. The polynucleotide sequence may be introduced at any locus within the genome of the microorganism provided that no vital function for growth of the microorganism and production of the fermentation product is affected.

As used herein the term "expression of a component is prevented or reduced" refers to an alteration in the genome of a microorganism, which interferes with the biosynthesis of such component or leads to the expression of a protein with an altered amino acid sequence whose function compared with the wild type counterpart with a non-altered amino acid sequence is completely or partially destroyed. The interference may occur at the transcriptional, translational or post-translational level. The alteration in the genome of the microorganism may be obtained e.g. by replacing through a single or double cross-over recombination a wild type DNA sequence by a DNA sequence containing the alteration. For convenient selection of transformants of the microorganism with the alteration in its genome the alteration may, e.g. be a DNA sequence encoding an antibiotic resistence marker or a gene complementing a possible auxotrophy of the microorganism.

Expression of a component of the respiratory chain may also be prevented or reduced by introduction of a DNA sequence complementary to the DNA sequence encoding the component at any genetic locus of the microorganism, so as to prevent or reduce the expres-sion of the component by an antisense mechanism.

As used herein, "target fermentation product" means a compound produced by fermenta-tion, such as for example riboflavin, pantothenic acid, biotin, thiamin, folic acid, pyrid-oxine, and amino acids.

As used herein, "cultivation of an aerobic microorganism to produce a target fermentation product" means that the microorganism is inoculated into a fermentation medium supplied with all the substrates required for growth of the organism and production of the fermentation product. The inoculated fermentation medium is subjected to certain physico-chemical parameters, such as temperature, pH and aeration, that will allow opti-mal biomass growth and product accumulation. These parameters vary from type to type of microorganism to be cultivated and from compound to compound to be produced. Procedures to empirically determine these parameters are well-known to those skilled in the art and include factorial plan or composite design. To further increase fermentation product accumulation substrates required for biomass growth or product formation may be supplied to the fermentation broth during the course of the cultivation of the micro-organism. For example, in the process according to the invention the microorganism may be subjected to fed-batch cultures with exponential and constant feeding profiles and chemostat cultures.

The fermentation process may be followed by analytically determining process parameters. For example, cell dry weight (cdw) may be determined, e.g., from cell suspensions that are harvested by centrifugation, washed with distilled water, and dried at, e.g. 110° C. for 24 h to a constant weight. Concentrations of carbon dioxide and oxygen in the bioreactor feed and effluent gas may be determined with, e.g., a mass spectrometer (e.g. Prima 600, Fisons Instruments). Glucose concentrations may be determined, e.g., enzymatically with, e.g., commercial kits (e.g. Beckman). Concentrations of organic acids, acetoin, and diacyl in the culture supernatant may be determined by, e.g., HPLC on a Supelcogel C610H column (4.6×250 mm) (Sigma) with, e.g., a diode array detector (Perkin Elmer). 0.2 N phosphoric acid may be used as mobile phase at a flow rate of 0.3 ml min-1 and 40° C. Target fermen-tation product concentrations may be determined by standard methods, e.g. riboflavin concentrations may be determined as, e.g., the absorption at 440 nm (A440) in cell-free culture broth. If A440 exceeds 0.6, the broth may be diluted with, e.g., 0.5 M potassium phosphate buffer (pH 6.8). If A440 exceeds 1.8, for example 0.8 ml of broth may be mixed with 0.2 ml of 0.2 M NaOH and diluted to an appropriate concentration with 0.5 M potas-sium phosphate buffer (pH 6.8).

The target fermentation product may be isolated from the microorganism and/or the me-dium. As used herein, the term "isolated" means that the target fermentation product is purified, or at least partially purified by methods including for example, filtration, centrifu-gation, and/or extraction. The target fermentation product may be further purified by re-crystallization from aqueous or organic solvents or applying other methods known in the art, such as for example, ion-exchange, size-exclusion, or hydrophobic interaction chroma-tography. For a detailed description of the procedures for isolation and purification of, e.g. riboflavin from a fermentation broth, see, e.g., EP 730,034.

The present invention further provides a polynucleotide, which polynucleotide is capable of preventing or reducing the expression of a less energy efficient component of the respi-ratory chain in a Gram positive host strain with alternative subchains of the respiratory chain. Preferably the Gram positive host strain is *B. subtilis* or *C. glutamicum* and the com-ponent of the respiratory chain, the expression of which is to be prevented or reduced, is the terminal oxidase encoded by cydAB. Preferably the polynucleotide has a nucleotide sequence which is illustrated as SEQ ID NO:1.

SEQ ID NO:1 may be modified at its 3' and 5' ends with extension sequences, each of which are several hundred base pairs in length, to increase the transformation efficiency of SEQ ID NO:1. The extension sequences are random sequences, which are preferably less than 80% homologous to DNA sequences of the recipient cells to prevent recombination at undesired loci. Such a polynucleotide sequence is then used to transform a micro-organism capable of producing a target fermentation product.

The polynucleotide sequence of the present invention may, e.g. comprise a DNA fragment from the cyd locus of *B. subtilis* or *C. glutamicum* provided with deletion-insertion muta-tions, e.g. as set forth in more detail in the examples. The two subunits of the cytochrome bd oxidase are encoded by cydA and cydB. In *B. subtilis* cydA and cydB comprise an operon together with cydC and cydD at 340o of the *B. subtilis* genome.

Another embodiment of the present invention is a *Bacillus subtilis* host cell or a Corynebac-terium glutamicum host cell transformed with a polynucleotide, which polynucle-otide is capable of preventing or reducing the expression of the cytochrome bd terminal oxidase of the respiratory chain in the host cell.

For example, a polynucleotide sequence encoding a cyd operon of *B. subtilis* with an in-serted antibiotic resistance gene that replaces 1376 bp from the 3' end of cydB and the 5' end of cydC may first be constructed in *E. coli*. Transformation of a natural competent *B. subtilis* microorganism with the polynucleotide sequence results in a *B. subtilis* mutant pro-vided with a cyd deletion. A PBS1 phage lysate prepared from this mutant may then be used to introduce via generalized transduction the cyd deletion into the production micro-organism RB50 containing multiple copies of the engineered rib operon pRF69. Standard recombinant DNA techniques may be used for the construction of the polynucleotide sequence and the *B. subtilis* mutants.

Transformants positive for the deletion-insertion mutation are selected using standard selection protocols. For example, the polynucleotide sequence used to transform the microorganism may include various selection markers, including for example antibiotic resistance markers, color producing markers, etc. Preferably, the marker is a neomycin resistance marker, and selection for the desired transformation includes identifying microorganisms capable of growing in fermentation media supplemented with neomycin, and which over-produce the target fermentation product, such as riboflavin.

Preferably the aerobic microorganism with increased efficiency of the respiratory chain is a recombinantly produced microorganism that over-produces riboflavin. As used herein, the term "over-produce" means that the microorganism produces the target fermentation pro-duct from a substrate that is used as a carbon source above at least 0.1% (w/w) yield, pre-ferably above 1% (w/w) yield, such as for example, above 4% (w/w) yield.

An example of such aerobic host cell is a riboflavin producing *B. subtilis* RB50 cell, designated as RB50::[pRF69]n containing multiple (n) copies (e.g., about 5 to about 20 copies) of pRF69 encoding a rib operon modified with the strong phage SPO1 promoter (P15) to enhance transcription of the rib genes. This recombinantly-produced micro-organism produces significantly more riboflavin than wild-type microorganisms.

*B. subtilis* RB50 was deposited with the Agricultural Research Culture Collection (NRRL), Peoria, Ill., under the terms of the Budapest Treaty on May 23, 1989, and was assigned accession number B 18502. Plasmid pRF69 was deposited with the American Type Culture Collection (ATCC), Rockville, Md., on Jun. 6, 1990, and was assigned accession number ATCC 68338.

The present invention also includes derivatives of RB50::[pRF69]. As used herein, a "deri-vative" of RB50::[pRF69] is any *B. subtilis* cell which contains the engineered rib operon of pRF69 or a polynucleotide sequence that is at least 25% identical to the engineered rib operon of pRF69, preferably at least 50% identical to the engineered rib operon of pRF69, and any other genetic modification, that leads to alterations in the expression of the ribo-flavin biosynthetic genes. In the present invention, the percent identity of the polynucleo-tide sequence are determined using the BLAST program and the server at the National Center of Biotechnology Information (Bethesda, Md., USA). A "derivative" of RB50::[pRF69] may also contain alterations in the genome of RB50::[pRF69], that affect the biosynthesis of compounds that are required as precursor compounds for riboflavin biosynthesis. Furthermore, auxotrophic RB50::[pRF69] mutants are also considered "derivatives" of RB50::[pRF69]. The term auxotrophic mutant refers to a microorganism that has been modified, by e.g. a mutation, to require the addition of an exogenous com-pound to grow, that prior to the mutation the microorganism could produce itself.

Accordingly, the present invention provides (1) a process for the preparation of a target fermentation product comprising cultivation of an aerobic microorganism to produce such product, wherein in the microorganism the efficiency of the respiratory chain is increased, preferably by introduction of a more energy efficient component or prevention or reduction of a less energy efficient component of a subchain, and the aerobic microorganism is a member of the bacterial genera *Escherichia, Bacillus, Cyanobacter, Streptomyces*, and *Corynebacterium*, preferably *E. coli, B. subtilis, B. amyloliquefaciens, B. licheniformis, B. ammoniagenes* or *C. glutamicum*;

(2) a process for the preparation of a target fermentation product, e.g. riboflavin, panto-thenic acid, biotin, thiamin, folic acid, pyridoxine, or an amino acid, comprising cultivation of an aerobic microorganism to produce such product, wherein in the microorganism the efficiency of the respiratory chain is increased;

(3) a polynucleotide, which polynucleotide is capable of preventing or reducing the expres-sion of a less energy efficient component of the respiratory chain, e.g. the terminal oxidase encoded by cydAB, in a Gram positive host strain, e.g. *B. subtilis* or *C. glutamicum*, with alternative subchains of the respiratory chain;

(4) a nucleotide sequence which is illustrated as SEQ ID NO:1 which is optionally modified at its 3'- and 5' ends with extension sequences, each of which are several hundred base pairs in length, and which extension sequences are random sequences, less than 80% homologous to DNA sequences of the recipient cells;

(5) a polynucleotide comprising a DNA fragment from the cyd locus of *B. subtilis* or *C. glutamicum* provided with deletion-insertion mutations;

(6) a *Bacillus subtilis* host cell or a *Corynebacterium glutamicum* host cell transformed with a polynucleotide, which polynucleotide is capable of preventing or reducing the expression of the cytochrome bd terminal oxidase of the respiratory chain in the host cell, e.g. wherein the polynucleotide sequence encodes a cyd operon of *B. subtilis* with an inserted antibiotic resistance gene that replaces 1376 bp from the 3' end of cydB and the 5' end of cydC, and optionally a further selection marker like an antibiotic resistance marker, e.g. neomycin resistance marker, or a color producing marker;

(7) a host cell as in (6) which is a recombinantly produced microorganism that over-pro-duces riboflavin;

(8) a host cell as in (6) wherein the microorganism produces the target fermentation pro-duct from a substrate that is used as a carbon source above at least 0.1% (w/w) yield, pre-ferably above 1% (w/w) yield, such as for example, above 4% (w/w) yield;

(9) a host cell as in (6) which is a *B. subtilis* RB50 cell, designated as RB50::[pRF69]n con-taining multiple (n) copies (for example about 5 to about 20 copies) of pRF69 encoding a rib operon modified with the strong phage SPO1 promoter (P15) to enhance transcription of the rib genes; and

(10) a host cell as in (6) which is a derivative of RB50::[pRF69], e.g. a *B. subtilis* cell which contains the engineered rib operon of pRF69 or a polynucleotide sequence that is at least 25% identical to the engineered rib operon of pRF69, preferably at least 50% identical to the engineered rib operon of pRF69.

The following examples are set forth to illustrate the processes, polynucleotides and host cells of the present invention. These examples are illustrative only and are not intended to limit the scope of the invention in any way. For example, the present invention may be varied by carrying out a fermentation process to produce a target fermentation product with any microorganism having a natural capability to utilize alternative respiratory chains wherein expression of a component of a respiratory chain is prevented. According to the present invention the process can be carried out as a continuous culture or as a batch or fed batch process in large scale industrial fermentors, varying the dilution rate from 0.3 l/h to 0.001 l/h, increasing the concentration of the components in the fermentation medium, or increasing glucose concentration up to 400 g/l. The media components and the re-quired physico-chemical parameters for all of these variations, would be determined and adjusted by one skilled in the art.

EXAMPLE 1

Construction of a Respiratory Mutant of *B. subtilis* RB50::pRF69 Carrying a cyd Deletion Construction of a cydBC deletion-insertion mutation: A 3.4 kb DNA fragment is amplified from DNA of *B. subtilis* microorganism 1012 [Saito et al., Mol. Gen. Genet. 170: 117-122 (1979)] using primers CydA+1 illustrated as SEQ ID NO:2 and CydC–1 illustrated as SEQ ID NO:3 and PCR reaction conditions of 30 cycles of denaturation at 95° C. for 1 min., annealing at 50° C. for 1 min. and extension at 72° C. for 4.5 min. The PCR product is puri-fied using the Wizard PCR purification kit (Promega Corp.). The PCR product is ligated into the pGEM-TEasy vector (Promega Corp.), resulting in plasmid pNMR20.

The 1.2 kb neomycin-resistance cassette from plasmid pBEST501 [Itaya et al., Nucl. Acids. Res. 17:4410 (1989)] is amplified using primers pBESTBcl+1 illustrated as SEQ ID NO:4 and pBESTBcl–1 illustrated as SEQ ID NO:5 using PCR reaction conditions as above. The amplified neomycin-resistant cassette is purified and digested with BclI, and is cloned into BclI-digested pNMR20 to give plasmid pNMR21 illustrated as SEQ ID NO:1 which contains the neo cassette inserted into cydBC in the same orientation as cyd transcription. Plasmid pNMR21 is linearised with PstI and transformed into *B. subtilis* wild-type strain 1012 and selected on TBAB plates containing neomycin to a final concentration of 5 mg×ml-1 to give *B. subtilis* microorganism NM18.

*B. subtilis* microorganism NM18 is used as a donor microorganism for preparation of PBS1 phage lysate. This lysate is used to transduce the riboflavin production microorganism RB50 provided with the modified riboflavin operon pRF69. RB50 refers to the host micro-organism of *B. subtilis*, which contains several mutations introduced to improve produc-tion of nucleotides and riboflavin. pRF69 refers to a rib operon modified by the introduc-tion of strong phage promoters which is introduced at the rib locus of pRF50. The modi-fied operon pRF69 is amplified to high copy numbers. A detailed description of the micro-organism RB50 and the modified rib operon pRF69 is presented EP 405,370. A number of neomycin-resistant colonies are obtained. Three of these clones are analyzed by PCR and Southern hybridization, and are shown to contain the cyd deletion. One of these clones is selected and renamed RB50::[pRF69] DcydBC. Southern blot hybridization reveals the pre-sence of pRF69.

RB50::[pRF69] DcydBC is cultivated in a rich, complex medium (VY medium: 25 g/l of Difco veal infusion plus 5 g/l yeast extract) supplemented with 10 mg/ml chloramphenicol to an optical density OD 660=1. One milliliter of this broth is transferred into 20 ml of VY medium supplemented with 30 mg/ml chloramphenicol and after reaching OD 1, again 1 ml of culture is transferred into 20 ml VY medium supplemented with 60 mg/ml chlor-amphenicol. The same passage is repeated using VY containing 80 mg/ml chlorampheni-col. After reaching an OD of 1, this culture is supplemented with 15% (Vol/Vol) glycerol and 1 ml aliquots are frozen at −80° C. The stepwise increase in the antibiotic concentra-tion is used to select for bacteria with increased copy number of the modified rib operon pRF69 (EP 405, 370).

EXAMPLE 2

Fed-batch Cultivation of RB50::[pRF69] DcydBC and the Parent Strain RB50::[pRF69]

For preparation of seed cultures aliquotes of the frozen RB50::[pRF69] DcydBC bacterial suspension of example 1 or the parent strain RB50::[pRF69] suspension are thawed and transferred into 100 ml VY medium supplemented with 80 mg/ml chloramphenicol. The cultures are incubated at 37° C. until reaching OD=10 (typically after 12 to 15 hours).

The main fermentation is initiated by inocculation of 50 ml of each of the seed cultures into 800 ml of a fermentation medium with the following composition (per liter of ddH2O): 27.3 g glucose×H2O; 0.75 g Na glutamate; 0.23 g NH4Cl; 1.41 g (NH4)2SO4; 4.11 g Na2HPO4×2H2O; 4.71 g KH2PO4; 4.71 g K2HPO4; 11.77 g yeast extract; 1 g MgSO4×7H2O; 62.5 mg CaCl2×2H2O; 40 mg FeSO4× 7H2O; 14.6 mg MnSO4×H2O; 4 mg ZnSO4×7H2O; 0.8 mg CuCl2×2H2O; 4 mg CoCl2×6H2O; 0.3 mg Na2MoO4× 2H2O; and 1 mg AlCl3×6H2O. A feed pump is switched on shortly before glucose is depleted indicated by a the drop in CO2 production. The feed medium (655.2 g glucose×H2O; 1.5 g MgSO4×7H2O; 11 mg MnSO4×H2O; and 3 mg ZnSO4×7H2O) is supplied at 13.3 mL L-1 h-1 for 2 hours after initiation of the feeding phase and then at 14.7 mL L-1 h-1. The fermentations are carried out in a 2 L LH discovery 210 series reactor (Adaptive Biosystems) at 39° C. The stirrer speed is set to 1,500 rpm and the air flow is kept between 3 and 5 L min-1, ensuring dissolved oxygen level above 15% throughout the cultivation.

EXAMPLE 3

Riboflavin Production with RB50::[pRF69] DcydBC and the Parent Strain RB50::[pRF69]

200 μl of a 0.2N NaOH solution is added to 0.8 ml of the fermentation samples of example 2 immediately after collection from the fermentation reactor. The sample is incubated for 20 seconds at room temperature to dissolve riboflavin crystals within the sample. An ali-quot of this suspension is diluted and neutralized with 0.5 molar potassium phosphate buffer pH 6.8. The samples are centrifuged in a table top Eppendorff centrifuge for 5 min at 14'000 rpm and the absorption at 440 nm (A440) in the supernatant is determined. The dilution of the samples is adjusted to achieve readings between 0.1 and 0.6 absorption units. The riboflavin concentration is calculated by comparing the absorption of the samples to those of riboflavin standards (Sigma, St. Luis, Mo., USA).

The results of this example show that upon introduction of the cyd deletion preventing the microorganism from using the cytochrome bd terminal oxidase subchain of the respiratory chain RB50::[pRF69] DcydBC produces 15.5 g/l riboflavin compared to 14.0 g/l of the parent strain RB50:: [pRF69] after 48 h of fermentation. At 24 hours of fermentation the advantage of the cyd deletion strain over the parent strain is even more pronounced with 9.8 g/l and 7.5 g/l, respectively.

The invention claimed is:

1. A process for the preparation of riboflavin comprising cultivation of a microorganism belonging to the genus *Bacillus* to produce riboflavin wherein the microorganism has mutation in cyd locus encoding cytochrome bd terminal oxidase, wherein said *Bacillus* has reduced cytochrome bd terminal oxidase activity and isolating the produced riboflavin.

2. An isolated nucleic acid comprising the nucleotide sequence of SEQ ID NO: 1.

3. An isolated polynucleotide according to claim 2 wherein SEQ ID NO:1 further comprises an extension sequence at its 3' end, at its 5' end, or at both its 3' end and its 5' end.

4. A *Bacillus subtilis* host cell transformed with a polynucleotide, which polynucleotide is capable of preventing or reducing the expression of the cytochrome bd terminal oxidase of the respiratory chain in the host cell, wherein the polynucleotide sequence encodes a cyd operon of *B. subtilis* with an inserted antibiotic resistance gene that replaces 1376 bp from the 3' end of cydB and the 5' end of cydC.

5. A host cell according to claim 4 which is a recombinantly produced microorganism that over-produces riboflavin.

6. An isolated nucleic acid comprising a cyd operon of *Bacillus subtilis*, wherein said cyd operon has a mutation within the cyd locus that when introduced into a host strain of the genus *Bacillus* is capable of preventing or reducing the expression of cytochrome bd terminal oxidase.

7. An isolated nucleic acid according to claim 3, wherein the extension sequences comprise at least 50 nucleotides.

8. A process according to claim 1, wherein the production of riboflavin is increased by at least 0.1% as compared to a wild type microorganism of the genus *Bacillus*.

* * * * *